United States Patent [19]

Ervin

[11] Patent Number: 5,021,351
[45] Date of Patent: Jun. 4, 1991

[54] PETRI DISH

[75] Inventor: Klon R. Ervin, Glen Arm, Md.

[73] Assignee: Becton, Dickinson and Company, Franklin Lakes, N.J.

[21] Appl. No.: 842,722

[22] Filed: Mar. 20, 1986

Related U.S. Application Data

[63] Continuation-in-part of Ser. No. 490,271, May 2, 1983, abandoned.

[51] Int. Cl.⁵ .......................... C12M 1/22; C12M 1/16
[52] U.S. Cl. .................................. 435/297; 435/298; 435/299; 206/508
[58] Field of Search ............... 435/287, 297, 298, 299, 435/300, 301; 206/508; 220/70

[56] References Cited

U.S. PATENT DOCUMENTS

| | | | |
|---|---|---|---|
| 2,254,168 | 8/1941 | Dale | 206/508 X |
| 2,992,974 | 7/1961 | Belcove et al. | 435/299 |
| 3,055,808 | 9/1962 | Henderson | 435/298 |
| 3,091,361 | 5/1963 | Gawron | 206/508 |
| 3,121,511 | 2/1964 | Whitehead | 206/508 X |
| 3,179,579 | 4/1965 | Harrison | 435/297 |
| 3,198,713 | 8/1965 | McCormick | 435/297 |
| 3,203,870 | 8/1965 | Andelin | 435/298 |
| 3,272,671 | 9/1966 | Gaylord et al. | 206/508 X |
| 3,449,825 | 3/1970 | Falcone et al. | 435/297 |
| 3,649,463 | 3/1972 | Buterbangh | 435/297 |
| 3,649,464 | 3/1972 | Freeman | 435/287 X |
| 3,684,660 | 8/1972 | Kereluk | 435/297 X |
| 3,729,382 | 4/1973 | Shaffer | 435/297 |
| 3,816,264 | 6/1974 | Winter et al. | 435/298 |
| 3,830,701 | 8/1974 | Stussman | 435/297 X |
| 3,870,602 | 3/1975 | Froman et al. | 435/299 X |
| 4,010,078 | 3/1977 | Taylor | 435/301 X |
| 4,051,951 | 10/1977 | Smith | 206/508 |
| 4,160,700 | 7/1979 | Boomus et al. | 435/298 |
| 4,321,330 | 3/1982 | Baker et al. | 435/298 X |

FOREIGN PATENT DOCUMENTS 1960113 10/1979 Fed. Rep. of Germany ...... 206/508

*Primary Examiner*—Esther M. Kepplinger
*Attorney, Agent, or Firm*—Richard E. Brown

[57] ABSTRACT

In accordance with the invention there is provided a Petri dish comprising a container for the growth of microorganism cultures and a lid for the container. The construction of the lid and the container provides an improved stacking feature when a plurality of Petri dishes are stacked. The container has improved features which provide a uniform media bed with more uniform depth and improved retention of the media.

21 Claims, 4 Drawing Sheets

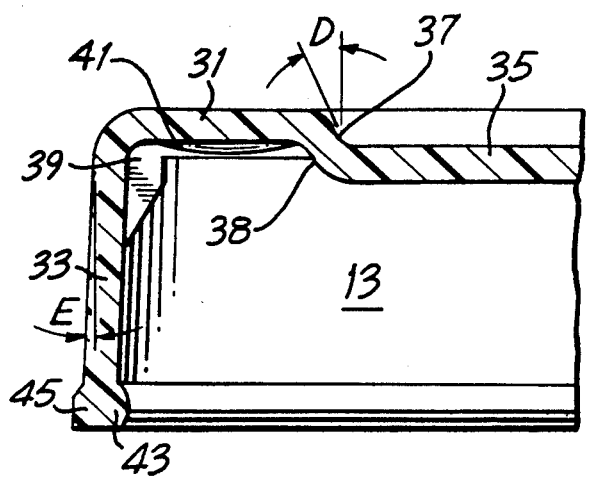("FIG. 3")
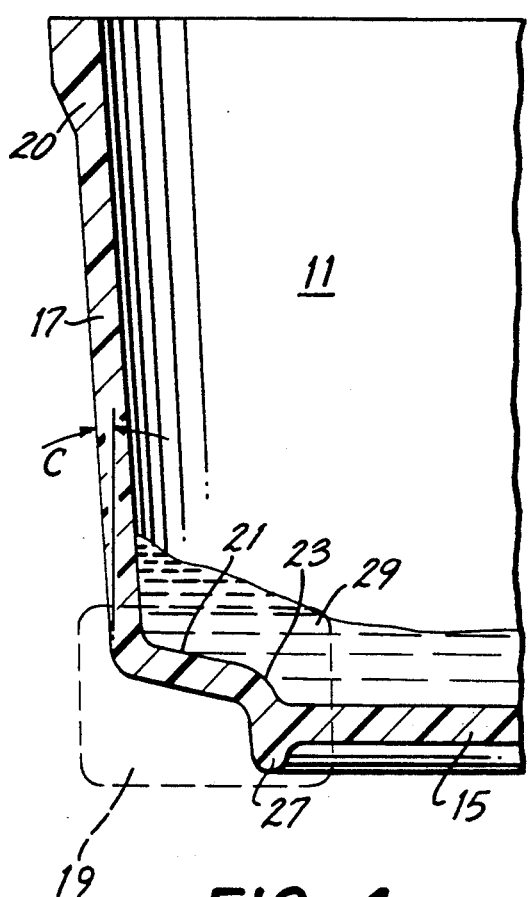("FIG. 4")
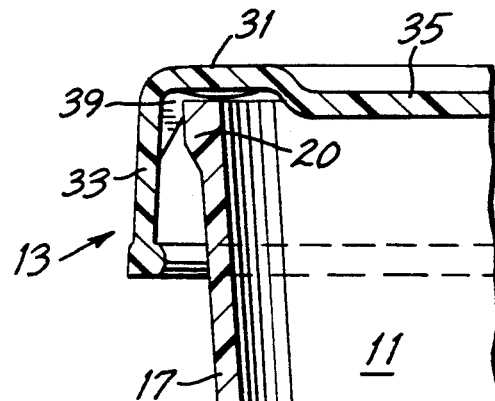
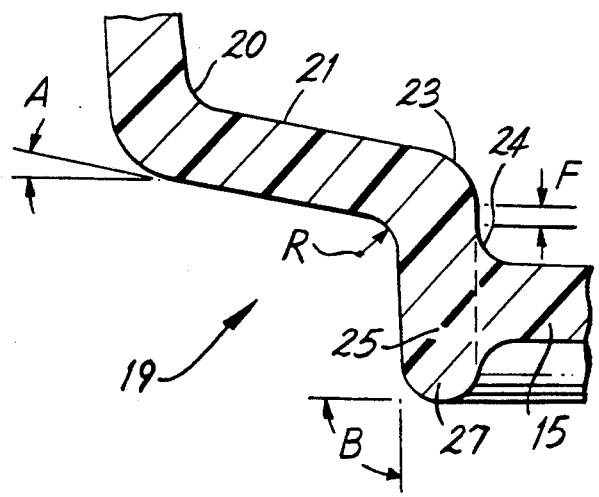("FIG. 4B")
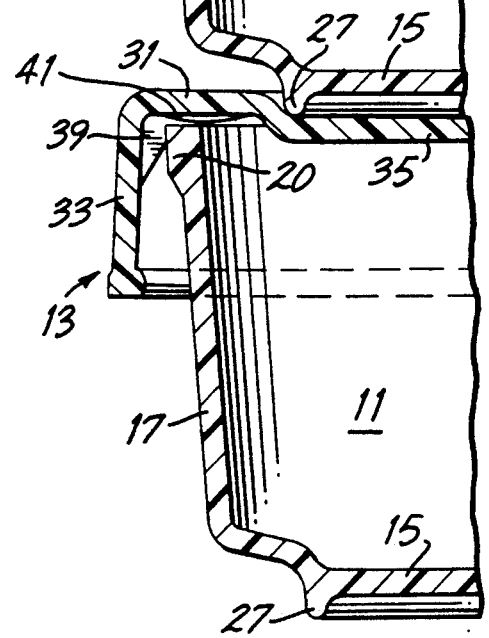("FIG. 8")

PETRI DISH

This application is a continuation-in-part of application Ser. No. 490,271, filed May 2, 1983, now abandoned.

BACKGROUND OF THE INVENTION

1. Field of the Invention

The present invention relates to an improved microorganism culturing dish, commonly referred to as a Petri dish. More particularly, the present invention is directed to a Petri dish with improved properties in respect to the ability to arrange one or more similar dishes to form a relatively stable stack of dishes, that is so structured and dimensioned as to enable a medical technician using the Petri dish to utilize the dish with increased efficiency and comfort, and has features which permit more efficient use of the media required to culture microorganisms.

Petri dishes generally consist of a bottom container for the medium which has a bottom wall and a single upstanding, cylindrical, peripheral side wall. The container is used in combination with a slightly larger lid having a top wall which merges into a downwardly extending cylindrical peripheral. The lid telescopically covers the container.

While the Petri dish is a seemingly simple product, it must meet many conflicting requirements of the manufacturer and the user. It is not uncommon that as many as a thousand Petri dishes are used by a technician in a single day. Efficient operations dictate that the technician must not have to use both hands to remove or replace the lid. Also it is common practice to work from an inverted stack of Petri dishes wherein the container is picked up with one hand, leaving the other hand free to streak a sample across a solidified media located in the bottom portion of the container.

It is also common practice for the laboratory technician to transport a stack of Petri dishes which have been inoculated from one portion of the laboratory to another. Accordingly, it is usual to provide some type of stacking restraint which prohibits sliding of the Petri dishes while they are being transported in a stack. A common practice is to provide a circumferential rib on the bottom of the container which mates with a circumferential rib of slightly larger or smaller diameter on the top of the lid of the Petri dish which is below the container in a stack. These mating ribs act to restrain movement of the Petri dish and prevent the stack from collapsing while it is being transported. Such arrangement of circumferential ribs has not been wholly satisfactory and has not completely prevented the problem of sliding while the stack of Petri dishes is carried.

A further problem is that, when solidified media is prepackaged in the bottom container, the solidified media tends to separate from the area adjacent to the junction of the side wall and the bottom wall of the bottom container during shipping and storage.

2. Prior Art

U.S. Pat. No. 4,160,700 to Boomus et al describes a Petri dish having an outwardly extending radial flange in the lid of a Petri dish to permit easy removal of the lid. The Boomus et al patent also discloses the use of a mating arrangement of circumferential ribs on the lid and container sections of the Petri dish which engage to inhibit sliding of a stack of Petri dishes. U.S. Pat. No. 3,198,713 to McCormick describes a Petri dish which is adapted to be arranged with one or more similar dishes to form a relatively stable stack of dishes. In the arrangement of the McCormick patent a plurality of open-top Petri dishes is arranged to form a stable stack wherein the base dish provides the lid for an underlying base dish. U.S. Pat. No. 3,649,463 to Buterbaugh describes a Petri dish having a bottom portion containing an outwardly extending peripheral flange provided with a plurality of inwardly extending slots. The flange is spaced upward from the bottom portion and away from the lower edge of the top portion to permit grasping of the flange by the fingers.

SUMMARY OF THE INVENTION

The present invention is directed to an improved Petri dish having an overall construction which facilitates easy stacking and transport. The improved Petri dish of the invention provides an improved ease in manipulation either through grasping the top lid of the Petri dish or the bottom container of the Petri dish for use by the laboratory technician in applying a specimen or sample to a solidified media contained in the bottom portion of the container.

In general, the Petri dish of the present invention has a transition zone at the bottom junction of the side wall and the bottom wall of the bottom container which increases the total area of the bottom container in contact with the media but does not reduce the overall thickness and depth of the solidified media. The formation of the transition zone includes an inclined straight section and predetermined radii at the various portions of the transition zone which facilitates the formation of a meniscus on the media as it solidifies and at the same time reduces media fallout during storage, handling and shipping, once the gelling agent in the media has solidified. The Petri dish of the present invention also includes an indentation in the lid of the Petri dish which permits plates to be stacked and provides improved stability of the stack during transportation. The indentation in the lid mates with a circumferential rib formed in the bottom wall of the container of the Petri dish.

DESCRIPTION OF THE DRAWINGS

FIG. 3 is an enlarged partial sectional view taken along line 3—3 of FIG. 2a.

FIG. 4 is an enlarged partial sectional view taken along line 4—4 of FIG. 2b.

FIG. 4b is further enlargement of the portion of FIG. 4 shown in dashed outline.

FIG. 6 is an enlarged partial sectional view taken through line 6—6 of FIG. 5a.

FIG. 8 shows the relationship of a stack of Petri dishes made in accordance with the present invention.

DETAILED DESCRIPTION OF THE INVENTION

Figure 1:
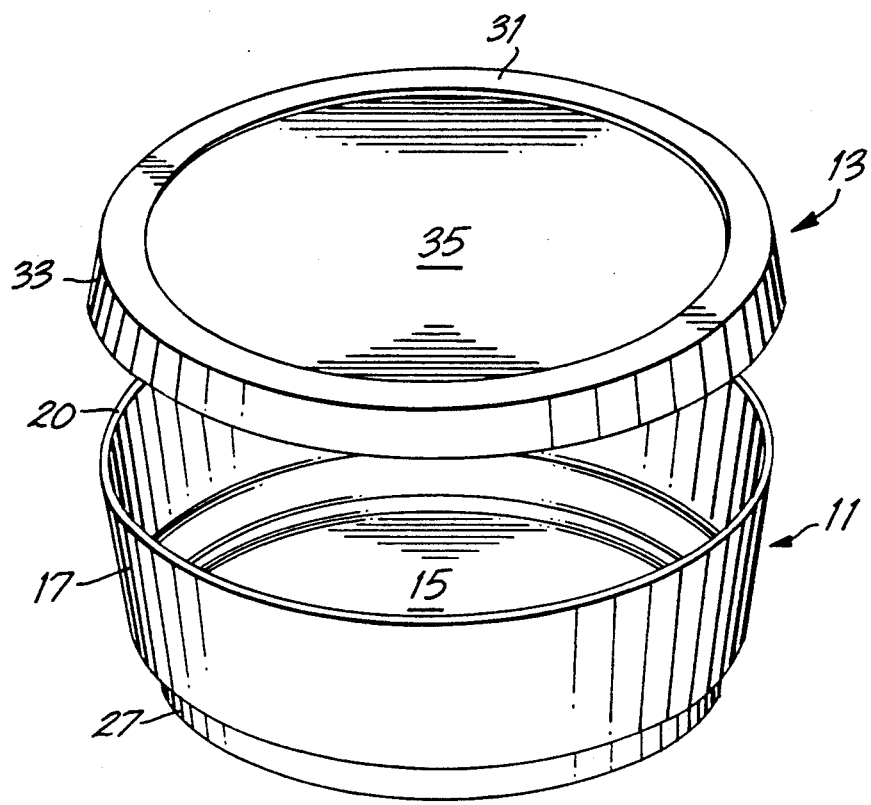
FIG. 1 is a perspective view of the Petri dish of the invention showing a lid and a container.
Figures 2A, 2B:
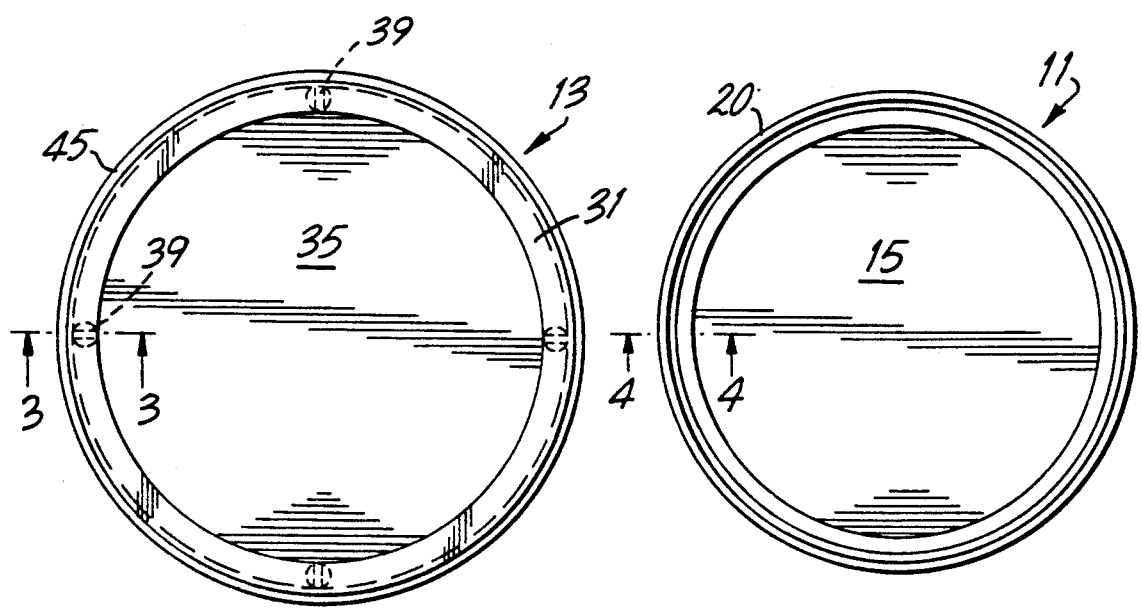
FIG. 2a is a top plan view of the lid of the Petri dish.
FIG. 2b is a top plan view of the container of the Petri dish.

Generally for culturing microorganisms, two types of medium are in common use: liquid medium in which the microorganisms settle on the bottom surface of the culture dish, and solidified medium in which the microorganisms are dispersed throughout the solidified culture medium. Solidified cultured medium is usually solidified through the use of a hydrocolloid, such as agar. The present invention is directed to Petri dishes which use solidified medium which is deposited in a bottom container of the Petri dish.

Referring now to the drawings, the Petri dish of the invention consists of a container 11 and a lid for the container. Both the container 11 and the lid 13 are of unitary molded construction and are formed from an organic polymer. At least the lid 13 should be transparent to enable inspection of the culture grown in the Petri dish and it is preferred that both the lid and the container be molded of a transparent polymer. Preferred polymers are polystyrene and polyparamethyl styrene. Other suitable polymers include polypropylene, polycarbonate, poly-vinylidene chloride, and styrene acrylonitrile.

The container has a flat, round bottom wall 15 from which there extends substantially perpendicularly upward a substantially cylindrical side wall 17. The side wall 17 merges into the bottom wall 15 through a transition zone 19. The enlarged upper section 20 of the side wall is provided for ease in releasing the molded container from the injection mold after the container is formed and cooperates with an arcuate portion of the lid 13 during automated assembly.

As shown in FIG. 4B, the transition zone 19 has a first substantially straight section 21 and a substantially curved section 18. The radius of curved section 18 is made as small as is consistent with injection molding practice. At curved section 18, straight section 21 merges with side wall 17 at an angle A which is preferably from about 1° to 5°, preferably about 3°, in relation to the plane of bottom wall 15. Straight section 21 merges into a second curved section 23, which has a radius of curvature R which is preferably from about 0.5 to 1.5 percent of the diameter of bottom wall 15, most preferably from about 0.17 to 0.9 percent. Second curved section 23 merges into a second straight sectio 25. The second straight section 25 is at an angle B, which is preferably substantially normal to the plane of the bottom wall 15, but may be from about 80° to about 90°. Angle B should not exceed about 92° to prevent interference during stacking of the container 11 and the lid 13. The second straight section 25 is substantially coincident with a portion of the bottom wall 15. Curved section 23 preferably merges into a third curved section 24 which is in turn merges into bottom wall 15. Preferably there is no distance F of straight section 25 between curved section 23 and third curved section 24. Distance F is preferably from 0 to about 1.0 mm. If distance F is more than about 1.0 mm the depth of solidified media 29 required to cover the transition zone 19 becomes too great and cracking of the media can occur.

The second straight section 25 extends downwardly from the bottom edge of the side wall 17 to provide a circumferential projection 27. This circumferential projection is concentric with the side wall 17 and is of less diameter than that of the side wall 17. The circumferential projection 27 is of arcuate cross section. The radius of the arc is not critical and is primarily provided for ease in molding of the container 11.

Figure 7:
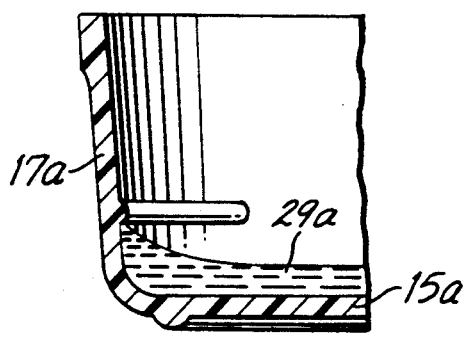
FIG. 7 is an enlarged partial sectional view taken along line 7—7 of FIG. 5b.

As shown in FIG. 4, the medium 29 forms an upwardly curving meniscus. It has been demonstrated that the construction of the container of the Petri dish of the present invention, having the transition zone 19, results in better media holding than the prior art containers wherein the side wall extends substantially downward till it merges with the bottom wall, such as shown in FIG. 7. Also, as shown in FIG. 4, the media has a substantially constant depth through the transition zone 19 which is the same as the depth of the media over the bottom wall 15. This results in a substantial alleviation of a "halo" effect.

The diameter of the container 11 at the top of side wall 17 is preferably from about 75 to about 100 millimeters. The total height of the container 11 from the top of the side wall 17 to the bottom of the circumferential projection 27 is preferably from about 10 to about 15 mm. Side wall 17 is usually inclined from a line normal to bottom wall 15 by an angle C for ease of removal from the mold. Angle C is preferably from about 0 to about 5 degrees, most preferably about 3°.

The portion of the side wall 17 immediately adjacent to the first straight section 21 of the transition zone 19 is preferably treated with an abrasive grit during the molding process to provide a frosted or abraded surface. The provision of an abraded surface at this portion of the side wall serves to aid in grasping the container in one hand of the laboratory technician.

As shown in FIG. 3, the lid 13 of the Petri dish has a flat, round top wall 31 which has extending substantially perpendicularly downwardly therefrom a substantially cylindrical side wall 33. The side wall 33 is usually inclined from a line normal to the top wall 31 by an angle E for ease of removal from the mold. Angle E is preferably from about 0 to about 5 degrees, most preferably about 3°. The depth of the side wall 33 is less than the height of side wall 17. Preferably the side wall 33 has a depth of from about 50 to about 60 percent of the depth of the container 11. For example, a preferred depth for the side wall 33 is 7.5 mm for a container depth of 13.33 mm.

The top wall 31 is provided with a depressed area 35. The edge 38 of the depressed area 35 is radially spaced from the side wall 33 a distance to receive the circumferential projection 27 of the container. This establishes a stackable feature which prevents the container from sliding away from the lid 13 when a stack of Petri dishes is prepared. The top wall 31 leads to the depressed area 35 through a straight edge section 37. The angle D that the edge section 37 makes with a line normal to the plane of the top wall 31 has been found to be important. This angle should be from about 10 to about 18 degrees, preferably about 15 degrees. Larger angles result in a failure of the combination of the depressed area 35 and the circumferential projection 27 to prevent sliding and a lessened angle results in reducing the ease of stackability of the Petri dishes of the invention.

A stacking lug 39 is provided at spaced intervals around the inside of top wall 31. The stacking lug serves to reduce the spacing between the side wall 17 of the container and the side wall 33 of the lid to prevent undue movement of the lid when in place over the container. The stacking lug 39 is provided in accordance with known practice which is generally shown and described in U.S. Pat. No. 4,321,330. The top portion 41 of the stacking lug 39 serves to raise the lid 13 from the container 11 when the lid 13 is in place. This provides a channel for air to pass between the lid and the container.

The side wall 33 terminates in an inner arcuate portion 43 and outer strengthening portion 45. The strengthening portion 45 provides additional bulk to assist in extracting the lid from the injection mold. The arcuate portion 43 is designed to assist in the automated assembly of the lid 13 with the container 11 by mechanical equipment.

A sequence of steps is shown in FIG. 9 which illustrates the use of the arcuate portion 43 of the lid 13 during automated assembly. The arcuate portion 43 provides a camming action to assist in locating lid 13 over the container 11 during such automated assembly through cooperation with the stiffened section.

FIG. 8 shows the relationship of the circumferential projection 27 and the depressed area 35 when a series of Petri dishes are placed in a stacked array. As shown, the circumferential projection 27 abuts the bottom of the depressed area 35 at the depressed area edge 37. The top 20 of the side wall 17 rests against the top portion 41 of the stacking lug 39. It should be noted that the depressed area 35 needs only to be wide enough to receive the circumferential projection 27 and does not need to extend across the full area of top wall 31, as shown.

Figure 6:
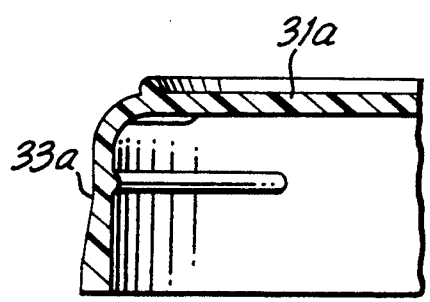
Figure 5A:
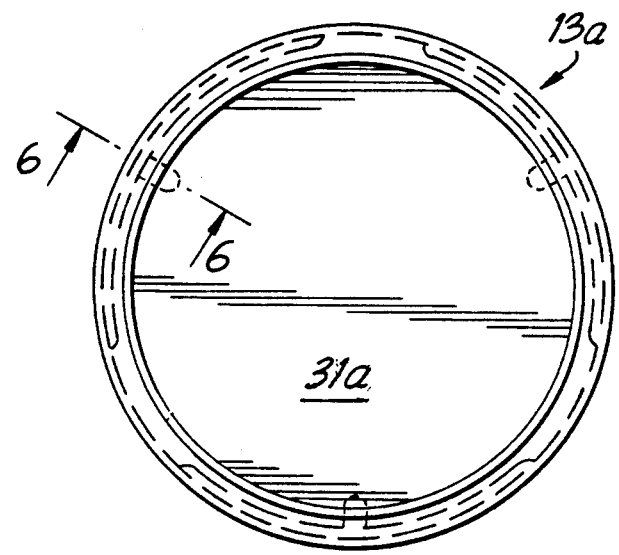
FIG. 5a is a top plan view of the lid of a prior art Petri dish.
Figure 5B:
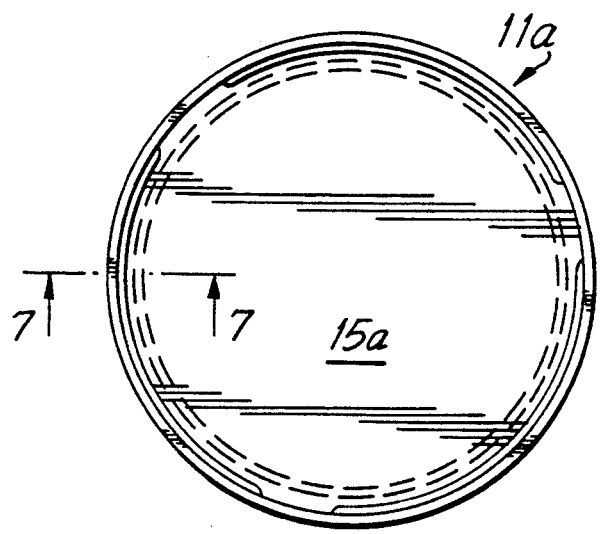
FIG. 5b is a top plan view of a container of a prior art Petri dish.
Figure 9A:
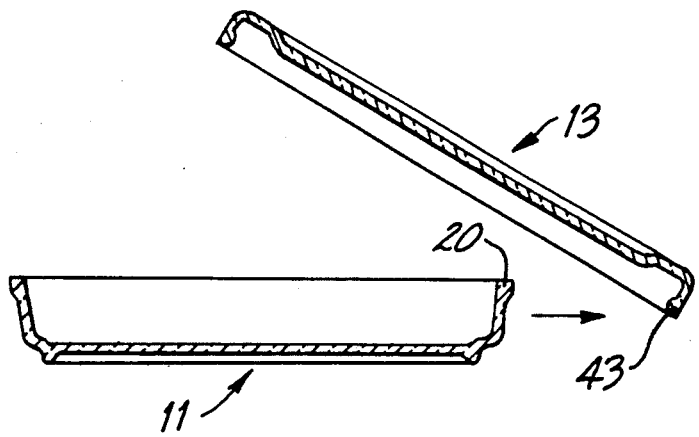
FIGS. 9a–9d are a sequence of schematic drawings illustrating an improved feature of the lid of the Petri dish of the invention which facilitates mating of the lid and the container of the Petri dish during manufacturing.
Figure 9B:
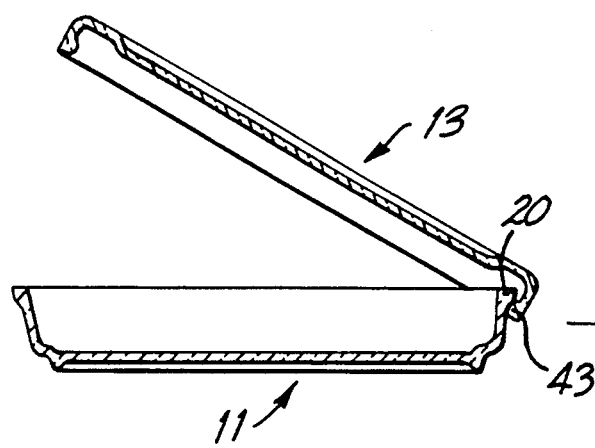
Figure 9C:
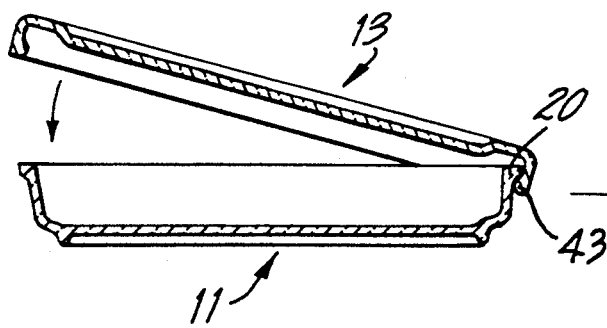
Figure 9D:
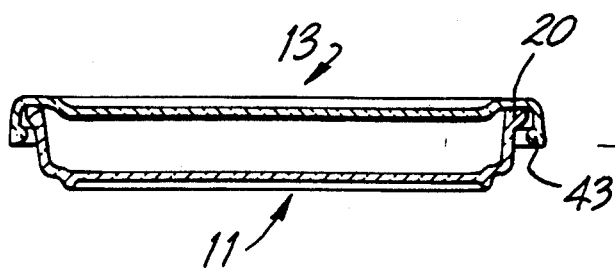

FIGS. 5, 6 and 7 illustrate a prior art Petri dish for comparative purposes. Elements of the prior art Petri dish which are common to the Petri dish of the invention are shown with common numbers and an "a" suffix.

The modifications made in the container lid of the Petri dish of the present invention provide a solution to numerous problems which have been present in the Petri dish industry for some time. While the invention has been described with respect to specific features of the invention numerous departures can be made from the specific description without departing from the spirit and scope of the present invention which is defined in the appended claims.

What is claimed is:

1. A Petri dish for the culturing of microorganisms comprising:
   a unitary bottom container having a substantially flat bottom wall merging into an upstanding, substantially cylindrical, side wall through a transition zone extending between the bottom wall and the side wall and a lid; said transition zone including first, second and third curved sections and first and second straight sections, said first curved section connecting said side wall and said first straight section, said second curved section connecting said first and second straight sections, said third curved section connecting said second straight section and said bottom wall, said first straight section extending from said side wall toward said bottom wall at a first angle relative to the plane of said bottom wall, said second straight section forming a second angle relative to the plane of said bottom wall, the lower terminus of said second straight section being substantially coincident with a portion of said bottom wall, said bottom wall having a projection on the bottom surface thereof.

2. A Petri dish in accordance with claim 1 wherein said first angle is from about 1° to about 5°.

3. A Petri dish in accordance with claim 1 wherein said first angle is about 3°.

4. A Petri dish in accordance with claim 1 wherein said second angle is from about 80° to about 90°.

5. A Petri dish in accordance with claim 1 wherein said second angle about 90°.

6. A Petri dish in accordance with claim 1 wherein the radius of curvature of said second curved section is from about 0.5 to about 1.5 percent of the diameter of said bottom wall.

7. A Petri dish in accordance with claim 1 wherein the radius of curvature of said second curved section is from about 0.7 to about 0.9 percent of the diameter of said bottom wall.

8. A Petri dish in accordance with claim 1 wherein said projection is provided by extending said second straight section beyond the junction of said second straight section with said bottom wall to provide a circumferential projection.

9. A Petri dish in accordance with claim 8 wherein said circumferential projection has an arcuate cross-section.

10. A Petri dish in accordance with claim 1 wherein the height of said container from the top of said side wall to the bottom of said bottom wall is from about 10 to about 15 mm.

11. A Petri dish in accordance with claim 1 which has a diameter at the top of said side wall of from about 75 to about 100 mm.

12. A Petri dish in accordance with claim 1 wherein said side wall is inclined to said bottom wall at a third angle from a line normal to said bottom wall of from about 0° to about 5°.

13. A Petri dish in accordance with claim 12 wherein said third angle is about 3°.

14. A Petri dish in accordance with claim 1 within the outside cylindrical surface of said side wall is abraded in an area extending upwardly from the junction of said side wall and transition zone.

15. A Petri dish in accordance with claim 1 having a lid which has a substantially flat top wall merging into a downwardly extending substantially cylindrical side wall having an inner cylindrical surface with a diameter larger than the diameter of said upwardly extending side wall of said container, said top wall merging through a straight slanted section to a depressed area which is radially spaced from said side wall of said lid a distance sufficient to receive said projection of said bottom container when a plurality of Petri dishes are stacked.

16. A Petri dish in accordance with claim 15 wherein said straight slanted section leads from said top wall to said depressed area at a fourth angle relative to a line normal to the plane of said top wall of from about 10° to about 18°.

17. A Petri dish in accordance with claim 16 wherein said fourth angle is 15°.

18. A Petri dish in accordance with claim 15 wherein the termination of the inner surface of said side wall of said lid has an arcuate projection.

19. A Petri dish in accordance with claim 15 wherein said side wall of said lid extends downwardly at a fifth angle normal to the plane of said top wall of from about 0° to about 5°.

20. A Petri dish in accordance with claim 19 wherein said fifth angle is about 3°.

21. A Petri dish for the culturing of microorganisms comprising:
   a unitary bottom container having a substantially flat bottom wall merging into an upstanding, substantially cylindrical, side wall through a transition zone extending between the bottom wall and the side wall and a lid; said transition zone including first, second and third curved sections and first and second straight sections, said first curved section connecting said side wall and said first straight section, said second curved section connecting said first and second straight sections, said third curved section connecting said second straight section and said bottom wall, said first straight section extending from said side wall toward said bottom wall at a first angle relative to the plane of said bottom wall, said second straight section forming a second angle relative to the plane of said bottom wall, the lower terminus of said second straight section being substantially coincident with a portion of said bottom wall, said bottom wall having a projection on the bottom surface thereof; said lid having a substantially flat top wall merging into a downwardly extending substantially cylindrical side wall having an inner cylindrical surface with a diameter larger than the diameter of said upwardly extending side wall of said container, said top wall merging through a straight slanted section to a depressed area which is radially spaced from said side wall of said lid a distance sufficient to receive said projection when a plurality of Petri dishes is stacked.

* * * * *